(12) United States Patent
Aguilar (10) Patent No.: US 12,161,344 B2
(45) Date of Patent: Dec. 10, 2024

(54) EXPANDABLE DEVICES FOR TREATING BODY LUMENS

(71) Applicant: Covidien LP, Mansfield, MA (US)

(72) Inventor: Julio Aguilar, Santa Clara, CA (US)

(73) Assignee: COVIDIEN LP, Mansfield, MA (US)

( * ) Notice: Subject to any disclaimer, the term of this patent is extended or adjusted under 35 U.S.C. 154(b) by 200 days.

(21) Appl. No.: 17/390,937

(22) Filed: Jul. 31, 2021

(65) Prior Publication Data

US 2022/0031334 A1     Feb. 3, 2022

Related U.S. Application Data

(60) Provisional application No. 62/706,117, filed on Jul. 31, 2020.

(51) Int. Cl.
*A61B 17/12* (2006.01)

(52) U.S. Cl.
CPC .. *A61B 17/12172* (2013.01); *A61B 17/12113* (2013.01)

(58) Field of Classification Search
CPC ........ A61B 17/12172; A61B 17/12113; A61B 2017/00526; A61B 2017/0084; A61B 2017/00867; A61B 2017/00942; A61B 17/12031; A61B 17/1214

See application file for complete search history.

(56) References Cited

U.S. PATENT DOCUMENTS

| | | | |
|---|---|---|---|
| 2011/0152993 A1* | 6/2011 | Marchand | A61B 17/12113 623/1.2 |
| 2018/0055515 A1* | 3/2018 | Greene, Jr. | A61B 17/12168 |
| 2018/0140305 A1* | 5/2018 | Connor | A61B 17/12118 |
| 2019/0192168 A1* | 6/2019 | Lorenzo | A61B 17/12113 |

* cited by examiner

*Primary Examiner* — Tuan V Nguyen
(74) *Attorney, Agent, or Firm* — Fortem IP LLP (57) ABSTRACT

Devices, systems, and methods for treating vascular defects are disclosed herein. One aspect of the present technology, for example, includes an occlusive device comprising an expandable mesh including an outer mesh and an inner mesh disposed within the outer mesh when the mesh is in an expanded, unconstrained state. The mesh may include a connection portion positioned at or within an inner cavity of the inner mesh and configured to be detachably coupled to a delivery member. The inner cavity may be configured to receive a distal portion of an elongated shaft and contain the distal portion while one or more coils is delivered through the elongated shaft into the inner cavity.

15 Claims, 6 Drawing Sheets

EXPANDABLE DEVICES FOR TREATING BODY LUMENS

CROSS-REFERENCE TO RELATED APPLICATION(S)

The present application claims the benefit of priority to U.S. Provisional Patent Application No. 62/706,117, filed Jul. 31, 2020, which is incorporated by reference herein in its entirety.

TECHNICAL FIELD

The present technology relates to expandable devices for treating body lumens. Particular embodiments are directed to intrasaccular occlusive devices for treating aneurysms.

BACKGROUND

Intracranial saccular aneurysms occur in 1% to 2% of the general population and account for approximately 80% to 85% of non-traumatic subarachnoid hemorrhages. Recent studies show a case fatality rate of 8.3% to 66.7% in patients with subarachnoid hemorrhage. Endovascular treatment of intracranial aneurysms emerged in the 1990s with the advent of the Guglielmi detachable coil system (Boston Scientific, Natick, MA), which includes packing the aneurysm sac with metal coils to reduce or disrupt the flow of blood into the aneurysm, thereby enabling a local thrombus or clot to form which fills and ultimately closes off the aneurysm. The use of coil embolization to treat aneurysms substantially increased after the publication of favorable clinical data, including evidence that disability or death at the 1-year follow-up occurred in 30.9% of patients treated surgically but only 23.5% in patients treated with coil embolization.[4] Similarly, these trials showed the overall morbidity and mortality at 1 year was 12.6% for surgical clipping and 9.8% for endovascular coiling (amongst patients with no prior history of subarachnoid hemorrhage).

Although coiling has proven to have better outcomes than surgical clipping for both ruptured and unruptured aneurysms, treating complex aneurysms using conventional coiling is challenging. This is especially true for wide-necked aneurysms. Coil segments may protrude from the aneurysm sac through the neck of the aneurysm and into the parent vessel, causing serious complications for the patient. To address this, some treatments include temporarily positioning a balloon within the parent vessel across the neck of the aneurysm to prevent the coils from migrating across the neck during delivery. Alternatively, some treatments include permanently positioning a neck-bridging stent within the parent vessel across the neck of the aneurysm to prevent the coils from migrating across the neck during delivery. While balloon-assisted or stent-assisted coiling for wide-neck aneurysms has shown better occlusion rates and lower recurrence than coiling alone, the recanalization rate of treated large/giant aneurysms can be as high as 18.2%. Moreover, the addition of a balloon or stent and its associated delivery system to the procedure increases the time, cost, and complexity of treatment. Deployment of the stent or balloon during the procedure also greatly increases the risk of an intraprocedural clot forming, and can damage the endothelial lining of the vessel wall. Permanently positioning a stent within the parent vessel increases the chronic risk of clot formation on the stent itself and associated ischemic complications, and thus necessitates the use of dual antiplatelet therapy ("DAPT"). DAPT, in turn, increases the risk and severity of hemorrhagic complications in patients with acutely ruptured aneurysms or other hemorrhagic risks. Thus, neck-bridging stents are not indicated for the treatment of ruptured aneurysms.

Accordingly, there is a need for improved devices and methods for treating aneurysms.

SUMMARY

The subject technology is illustrated, for example, according to various aspects described below, including with reference to FIGS. 1-4E. In some embodiments, the device comprises an occlusive device for treating an aneurysm. The device can comprise an expandable mesh having a proximal end portion, a distal end portion, a first mesh, and a second mesh. The first mesh can define a first cavity therein and include a proximal end portion and a distal end portion. The second mesh can define a second cavity therein and have a proximal end portion and a distal end portion. The second mesh can be configured to be disposed within the first cavity when the expandable mesh is deployed within the aneurysm. The device may further comprise a connection portion disposed at the distal end portion of the second mesh. The connection portion can be configured to detachably couple the expandable mesh to a delivery member. The proximal end portion of the first mesh and the proximal end portion of the second mesh can be continuous at a fold at the proximal end portion of the mesh that surrounds an opening. The mesh can have a low-profile state for intravascular delivery to the aneurysm and an expanded state. When the expandable mesh is implanted within the aneurysm in the expanded state, the second cavity can be configured to receive and contain a coil therein. In several of such embodiments, the connection portion can be disposed at least partially within the second cavity, extend into the second cavity, and/or be disposed completely within the second cavity. According to some aspects of the technology, a distal surface of the second mesh can include a depression that is concave towards the first cavity. In some embodiments, the opening is configured to receive an elongated shaft therethrough. The elongated shaft can be configured to receive the delivery member therethrough. In some embodiments, at least when the expandable mesh is in an expanded, unconstrained state, the distal end portion of the second mesh is spaced apart from the distal end portion of the first mesh such that the second end portion of the second mesh is free to axially stretch and compress independent of the first mesh. In some embodiments, when the expandable mesh is positioned within the aneurysm, the opening is aligned with the neck of the aneurysm. According to several embodiments, the first and/or second meshes are generally ball-shaped. In some embodiments, the proximal end portion of the expandable mesh does not include a hub. In some embodiments, the device optionally comprises a flexible member coupled to the distal end portion of the expandable mesh. In several of such embodiments, the flexible member can be a coil that is coupled to the distal end portion of the first mesh and extend away from the first cavity. Additionally or alternatively, the coil can be coupled to the distal end portion of the second mesh and extend away from the second mesh within the first cavity. According to several embodiments, the coil has a first end coupled to the distal end portion of the second mesh and a second end coupled to the proximal end portion of the first mesh.

The present technology can include a device comprising a proximal end portion and a distal end portion, where the proximal end portion comprises a proximal surface having an opening therethrough. The device can further comprise an outer mesh defining an outer volume and an inner mesh defining an inner volume. The outer and inner meshes meet can meet at the opening. The device can further include a connector positioned at least partially within the inner volume at a location spaced apart from the proximal end portion of the device. The device can have a low-profile state for intravascular delivery to the aneurysm and an expanded state in which the inner mesh is disposed within the outer volume. According to several embodiments, when the occlusive device is implanted within the aneurysm in the expanded state, the inner mesh is configured to receive a coil within the inner volume. In any case, the connector can extend into the inner volume and/or be disposed completely within the inner volume. According to several examples, a distal surface of the inner mesh comprises a recessed portion. In some embodiments, the opening is configured to receive an elongated shaft therethrough. At least when the device is in an expanded, unconstrained state, a distal end portion of the inner mesh can be spaced apart from a distal end portion of the outer mesh such that the distal end portion of the inner mesh is free to axially stretch and compress independent of the outer mesh. When the device is positioned within the aneurysm, the opening can be aligned with the neck of the aneurysm. In some embodiments, the inner and/or outer meshes are generally ball-shaped. In some embodiments, the proximal end portion of the device does not include a hub. Optionally, the device can comprise a flexible member, such as a coil, suture, wire, or other member, coupled to the distal end portion of the device. The coil can be coupled to a distal end portion of the outer mesh and extend away from the outer volume. In some embodiments, the coil is coupled to a distal end portion of the inner mesh and extends away from the inner mesh within the outer volume. In several of such embodiments, the coil can have a first end coupled to the distal end portion of the inner mesh and a second end coupled to a proximal end portion of the outer mesh.

The present technology includes methods for treating an aneurysm. According to several examples, the method comprises intravascularly delivering an expandable mesh to the aneurysm in a low-profile state within an elongated shaft, where the expandable mesh is detachably coupled at a connection portion to an elongated member extending through the elongated shaft. The method may continue with deploying the expandable mesh within the aneurysm, where the expandable mesh comprises an outer mesh defining an outer cavity and an inner mesh disposed within the outer mesh. The inner mesh can define an inner cavity. In some embodiments, the connection portion is positioned at the inner mesh. The method can include detaching the expandable mesh from the elongated member while the elongated shaft is positioned within the inner cavity, and delivering an embolic coil through the elongated shaft to the inner cavity. In some embodiments, a plurality of embolic coils can be delivered through the elongated shaft to the inner cavity. According to several examples, deploying the expandable mesh within the aneurysm comprises pushing the outer mesh distally from the elongated shaft into the aneurysm cavity and, after the outer mesh has at least partially expanded within the aneurysm cavity, pushing the inner mesh distally from the elongated shaft such that the inner mesh expands within the outer cavity of the outer mesh. The method can further comprise withdrawing the elongated shaft from a first position within the inner cavity to a second position within the inner cavity. The method can further comprise withdrawing the elongated shaft from the inner cavity through an opening defined by a fold formed by a meeting of the inner and outer meshes.

The present technology includes methods for making an occlusive device configured to be implanted within an aneurysm. According to several examples, the method comprises threading a first fixture over a tubular braid such that the tubular braid has a first portion proximal of the first fixture, a second portion within the first fixture, and a third portion distal of the first fixture. The third portion of the braid can then be inverted proximally over the first fixture and the first portion. The inverted third portion can comprise a fourth portion positioned over the first fixture and a fifth portion positioned over with the first portion. The method can further comprise threading a second fixture over the first and fifth portions and positioning the fourth portion between the second fixture and the first fixture. The fifth portion of the braid can then be inverted distally over the second fixture. While the fifth portion of the braid is inverted over the second fixture, the braid can be heat treated. According to several examples, the method includes positioning a third fixture over the fourth portion such that the fourth portion is positioned between the third fixture and the first fixture. In some embodiments, inverting the fifth portion includes inverting the fifth portion over the second fixture and the third fixture.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology is directed generally to devices, systems, and methods for the treatment of vascular defects, and in particular, to endosaccular occlusive devices for treating intracranial wide-neck aneurysms. The occlusive devices of the present technology, for example, include a self-expanding mesh structure comprising outer and inner nested meshes. When the mesh structure is implanted in the aneurysm, the outer mesh conforms to the shape of the aneurysm cavity to anchor the device within the cavity while the inner mesh surrounds the distal portion of the delivery catheter and prevents migration of the delivery catheter out of the aneurysm. The inner mesh continues to contain the delivery catheter within the aneurysm sac as one or more coils are delivered into the interior of the inner mesh through the delivery catheter. Accordingly, the mesh structures of the present technology provide predictable placement of embolic coils within the aneurysm without the aid of an additional device (such as a stent) in the parent vessel, thus avoiding the attendant disadvantages plaguing conventional endovascular aneurysm treatment devices, such as the inability to treat wide neck aneurysms and necessitating a DAPT regimen.

Figure 1:
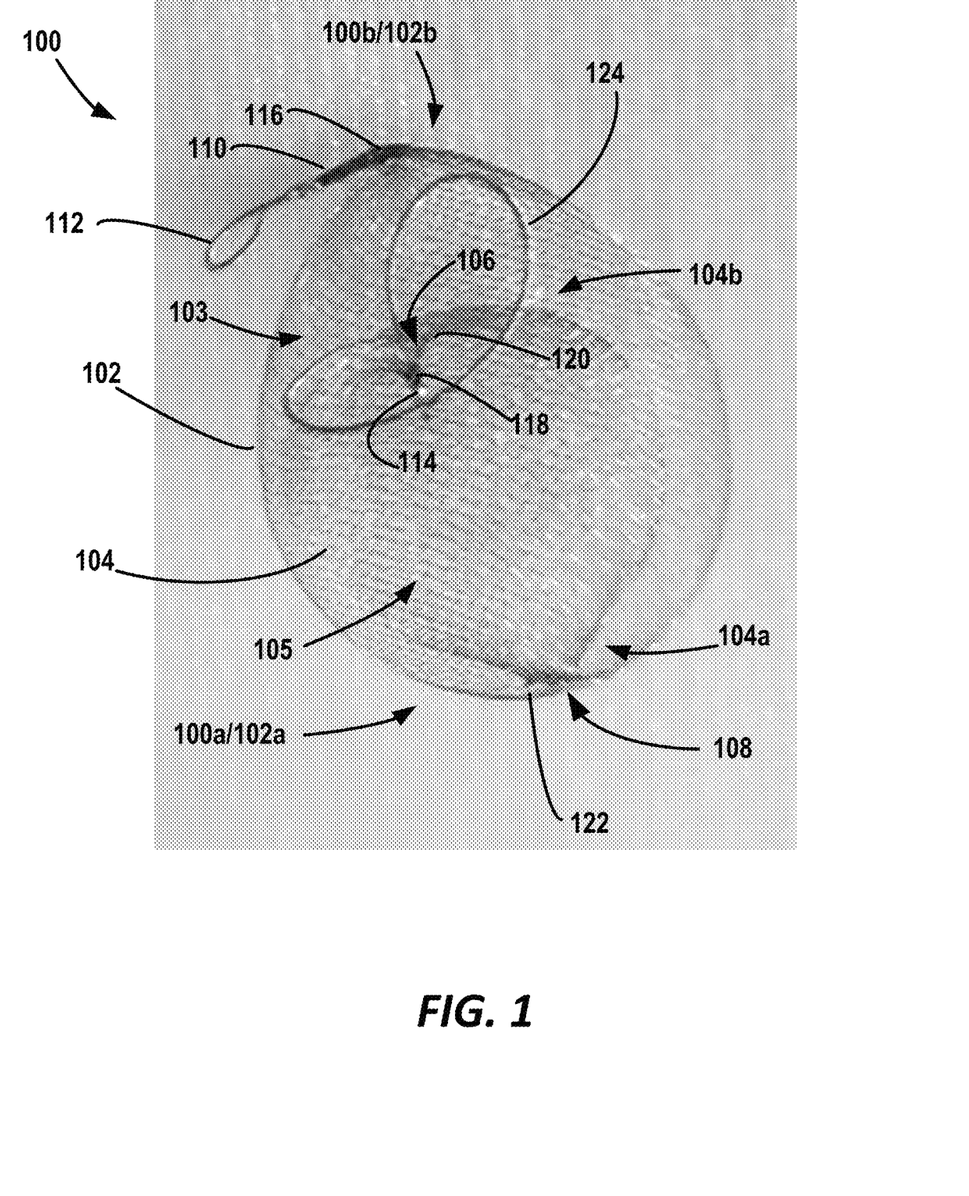
FIG. 1 shows an occlusive device configured in accordance with several embodiments of the present technology.

FIG. 1 depicts an occlusive device 100 (or "device 100") configured in accordance with several embodiments of the present technology, shown in an expanded, unconstrained state. The occlusive device 100 may comprise an expandable mesh structure configured to be implanted within an aneurysm, such as a cerebral aneurysm. As shown in FIG. 1, the mesh has a proximal end portion 100a and a distal end portion 100b and comprises first and second meshes 102, 104. The first mesh 102 can surround and define a first cavity 103 and have a proximal end portion 102a and a distal end portion 102b. In use, the first mesh 102 can be configured to expand into apposition with the aneurysm wall and conform to the shape of the aneurysm. The second mesh 104 can surround and define a second cavity 105, and has a proximal end portion 104a and a distal end portion 104b. The proximal end portion 102a of the first mesh 102 can be coupled to the proximal end portion 104a of the second mesh 104 at a joint 122. As shown in FIG. 1, at least when the device 100 is in an expanded, unconstrained state, the second mesh 104 is configured to be disposed within the first cavity 103 of the first mesh 102. In some embodiments, the joint 122 is disposed at the proximal end portion 100a of the device 100 such that, when implanted in an aneurysm, the joint 122 is positioned at or near the neck of the aneurysm. The device 100 can further comprise an opening 108 at the proximal end portion 100a, as detailed below.

In some embodiments, for example as shown in FIG. 1, the distal end portion 102b of the first mesh 102 comprises a distal tail that extends away from the main device and/or first mesh body. Additionally or alternatively, the device 100 includes a soft, atraumatic lead-in member 112 (such as a coil) at the distal end portion 100b. The lead-in member 112 can be coupled to the distal end of the distal tail, for example via a connector band. In some embodiments, the lead-in member 112 is coupled directly to the globular body of the first mesh 102. In some embodiments, the device 100 does not include a distal tail and terminates at or near the rounded distal end portion 102b of the first mesh 102. In these and other embodiments, the device 100 does not include a lead-in member 112 and terminates at or near the distal end of the distal tail or the rounded distal end portion 102b of the first mesh 102.

The device 100 may further comprise a connection portion 114 configured to detachably couple the expandable mesh to a delivery member. The connection portion 114 may be disposed, for example, at the distal end portion 104b of the second mesh 104. In some embodiments, all or a portion of the connection portion 114 is disposed within the second cavity 105. As such, when the delivery system is coupled to the device 100, a distal end portion of the delivery member and/or delivery catheter are positioned within the second cavity 105. Detachment of the device 100 can thus occur at a location distal of the aneurysm neck and/or distal of a proximal end portion 100a of the device 100. In some embodiments, the second mesh 104 includes a depression 106 at the distal end portion 104b that is aligned with the connection portion 114.

The first mesh 102 can be biased to expand to a preset shape. For example, the first mesh 102 can be formed of a resilient and/or superelastic material that has been heat treated such that, upon release from the constraints of a delivery catheter, the first mesh 102 self-expands to a predetermined shape. The first mesh 102 can remain sufficiently compliant, however, to conform to the shape of the aneurysm when implanted. In some embodiments, the first mesh 102 has a globular shape in an expanded, unconstrained configuration. Additionally or alternatively, the second mesh 104 can be biased to expand to a preset shape. For example, the second mesh 104 can be formed of a resilient and/or superelastic material that has been heat treated such that, upon release from the constraints of a delivery catheter, the second mesh 104 self-expands to a predetermined shape. In some embodiments, the second mesh 104 has a globular shape in an expanded, unconstrained configuration. The second mesh 104 can remain sufficiently compliant, however, such that its walls can expand and/or change shape in response to outward forces applied by embolic material (e.g., coils, a liquid embolic, etc.) delivered into the second cavity 105, as detailed below.

The first and second meshes 102, 104 can have the same or different shapes, and can have the same or different sizes. In some embodiments, the first mesh 102 is oversized relative to the second mesh 104 such that, when deployed in an aneurysm, the first mesh 102 presses outwardly against the aneurysm wall and anchors the device 100 within the aneurysm while the second mesh 104 floats within the first cavity 103, at least when first deployed. For example, the device 100 can be configured such that substantially all of the outer surface of the second mesh 104 is spaced apart from the aneurysm wall and/or the first mesh 102 when the device 100 is in an expanded configuration (within or outside of an aneurysm). Accordingly, the distal end portion 104b of the second mesh 104 is free to axially stretch and compress independent of the first mesh 102.

The second mesh 104 can be configured such that the outwardly-directed forces applied by embolic material in the second cavity 105 pushes the wall of the second mesh 104 radially outwardly, towards the wall of the first mesh 102 and/or aneurysm wall. In some embodiments, the delivered embolic material causes the second mesh 104 to contact the first mesh 102. In any case, the additional forces generated by the second mesh 104 and/or embolic material provides the device 100 with improved wall apposition and prevents the device from being pushed distally (further into the aneurysm sac) as a result of blood flow/pressure in the parent vessel, thus reducing and/or eliminating the risk of recanalization.

According to several methods of use, the opening 108 at the proximal portion 100a is configured to expand and/or change shape as the second mesh 104 expands and/or changes shape in response to the delivery of embolic material. For example, a cross-sectional dimension of the opening 108 can increase or decrease in response to proximally, distally, and/or laterally directed forces (towards or away from the cavities) applied to the first and/or second meshes 102, 104. This is because the first and second meshes 102, 104 are continuous with one another at the opening 108, thus allowing the device 100 to dynamically adjust the surface areas (and volumes) of the first and second meshes 102, 104 in response to forces applied on the first and/or second meshes 102, 104 by the surrounding aneurysm wall and the embolic material as it fills the second cavity 105.

In some embodiments, when the device 100 is in an expanded, unconstrained configuration, all or a portion of the second mesh 104 contacts and/or presses outwardly against an inner surface of the first mesh 102. When such embodiments are deployed in an aneurysm, the second mesh 104 contacts the first mesh 102 even without the presence of embolic material. Embolic material can then be delivered to the second cavity 105 to improve the wall apposition and supplement the existing radially outward force.

Figure 2:
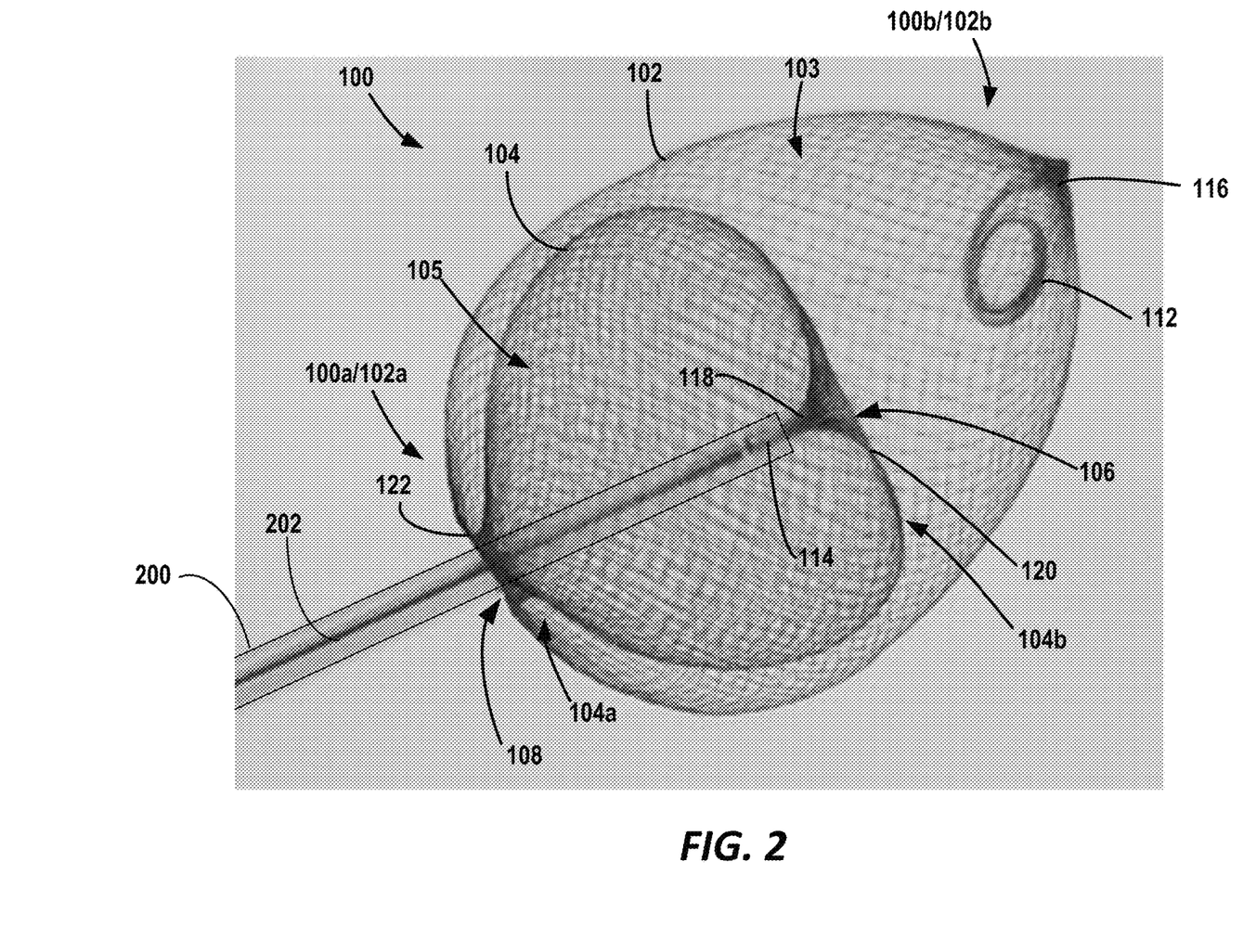
FIG. 2 is an occlusive device configured in accordance with several embodiments of the present technology, shown coupled to a delivery system.

In some embodiments, the opening 108 at the proximal end portion 100a of the device 100 can be configured to receive a delivery device therethrough. For example, FIG. 2 shows the device 100 coupled to an example delivery device comprising an elongated shaft 200 and an elongated manipulation member 202. The manipulation member 202 can be slidably positioned within the shaft 200. The device 100 can be configured to be compressed and/or constrained in a low-profile state within the shaft 200 during intravascular delivery to the aneurysm. To deploy the device 100, the device 100 can be released from the constraints of the shaft 200, for example by withdrawing the shaft 200 proximally relative to the device 100 and/or advancing the device 100 distally beyond the shaft 200. The connection portion 114 of the device 100 can be configured to be detachably coupled to a distal end portion of the manipulation member 202. Once the device 100 is deployed within the aneurysm, the device 100 can be mechanically or electrolytically released from the distal end of the manipulation member 202. The manipulation member 202 can then be withdrawn while leaving the shaft 200 positioned through the opening 108 (within the second cavity 105), and embolic material (not shown) can be delivered through the shaft 200 into the second cavity 105 to fill and occlude the second mesh 104. Thus, the opening 108 provides a means for keeping the shaft 200 within the second cavity 105 so that the embolic material is delivered directly into an interior region of the second mesh 104 to fill and secure the neck region of the aneurysm.

As previously mentioned, the first and second meshes 102, 104 may come together proximally at the annular edge of the opening 108. For example, in some embodiments the first and second meshes 102, 104 may be formed of the same tubular braid that has been inverted so as to form an inner layer and an outer layer. In such cases, the first and second meshes 102, 104 may be continuous at an everted portion 121 surrounding the opening 108. Prior to being deformed to form the device 100, the tubular braid has first and second ends 118, 110. When formed into the device 100, the first end 118 of the braid is disposed within the second cavity 105 of the second mesh 104. The braid then extends distally until everting at rounded surface 120, then extends proximally to the opening 108, then everts again (at everted portion 121) and extends distally to the second end 110 proximate the lead-in member 112. The once-tubular braid can be compressed and/or crimped at the second end 110, thereby forming a narrowed distal tail. The distal tail can be coupled to the lead-in member 112 by a connector, such as a tubular band. In some embodiments, the tubular band may be radiopaque. To help guide the device across the neck of the aneurysm during deployment, in some embodiments the device 100 may comprise a preset bend 116 in the mesh tail between the distal end portion 102b of the first mesh 102 and the atraumatic lead-in member 112, as shown in FIG. 1.

Figure 3A:
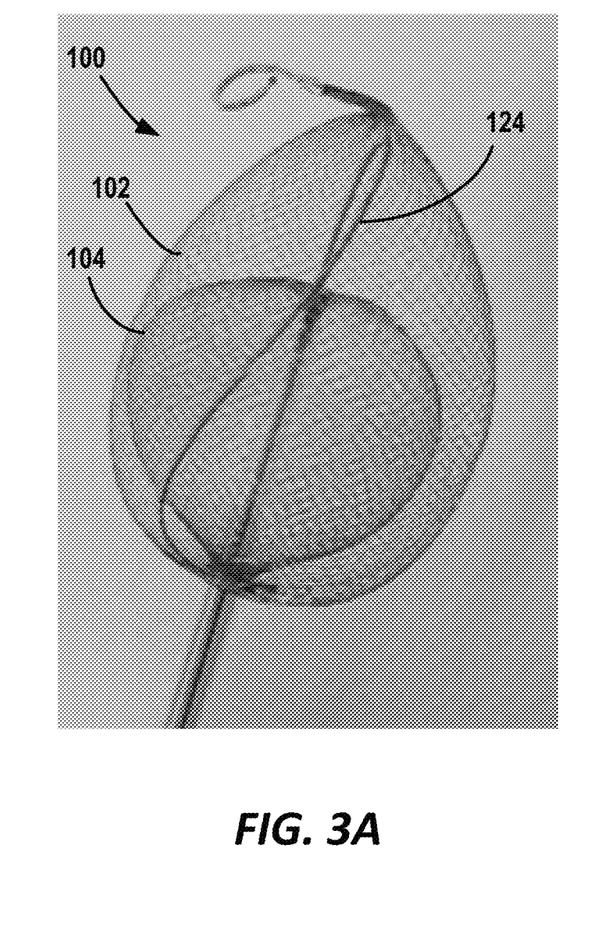
FIGS. 3A and 3B are different views of an occlusive device configured in accordance with several embodiments of the present technology.
Figure 3B:
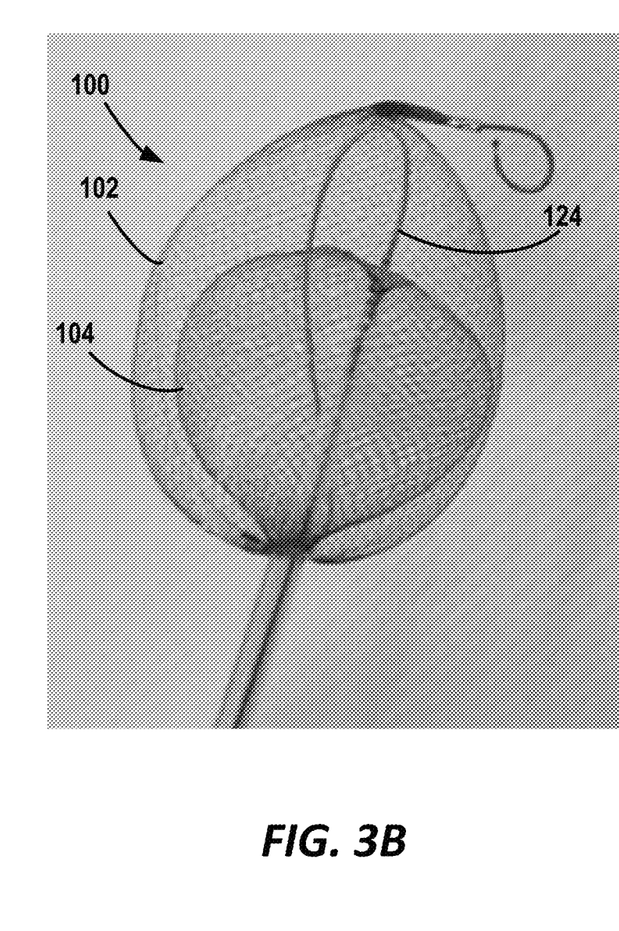

In some embodiments, the device 100 may comprise a flexible inner member 124 coupled to and extending distally away from the distal end portion 104b of the second mesh 104. The inner member 124 can be completely contained within the first cavity 103, between the second mesh 104 and the first mesh 102. The inner member 124 can be, for example, a coil, a braid, a wire, and/or other flexible member. The inner member 124 can help position the second mesh 104 relative to the first mesh 102 upon deployment. For example, the inner member 124 can be configured to space a distal end portion 104b of the second mesh 104 from the distal end portion 102b of the first mesh 102. In some embodiments, the inner member 124 has a first end coupled to the connection portion 114 and a free second end disposed between the first and second meshes 102, 104. In some embodiments, for example as shown in FIGS. 3A and 3B, the inner coil 124 can have a first end coupled to the connection portion 114 and a second end coupled to the proximal end portion of the first mesh 102. In some embodiments, the device 100 does not include an inner coil 124.

The device 100, first mesh 102, and/or second mesh 104 may have a shape and/or configurations that depends on the geometry of the aneurysm to be treated. For example, the device 100, first mesh 102, and/or second mesh 104 can comprise spherical and non-spherical shapes, cylinders, hemispheres, polyhedrons (e.g., cuboids, tetrahedrons (e.g. pyramids), octahedrons, prisms, etc.), oblate spheroids, plates (e.g., discs, polygonal plates), bowls, non-spherical surfaces of revolution (e.g., toruses, cones, cylinders, or other shapes rotated about a center point or a coplanar axis), and combinations thereof. In its expanded state, the device 100 may have a size and shape suitable for fitting snugly within a vascular cavity or vesicle (e.g., an aneurysm, or perhaps, a fistula). In some embodiments, the device 100 may comprise more than two mesh members which when relaxed and in the expanded configuration nest concentrically, or non-concentrically, with each other within the vascular cavity.

In those embodiments where the mesh comprises a braid formed of a filament or a plurality of filaments, the filament or filaments may comprise one or more wires, at least some of which (e.g., 25% of the wires, 50% of the wires, 80% of the wires, 100% of the wires, etc.) are made of one or more shape memory and/or superelastic materials. Some or all of the wires may have a diameter between about 0.0010 inches and about 0.0012 inches, about 0.0010 inches, about 0.0011 inches, 0.0012 inches (at least prior to etching). In some embodiments, some or all of the wires may be drawn-filled tubes ("DFT") having a radiopaque core (e.g., platinum) surrounded by a shape memory alloy and/or superelastic alloy (e.g., Nitinol, cobalt chromium, etc.).

All or a portion of the length of some or all of the filaments comprising all or a portion of the first and/or second mesh 102, 104 may have one or more coatings or surface treatments. For example, the filaments may have a lubricious coating or treatment that reduces the delivery force of the device 100 as the device 100 is advanced through the delivery catheter. In some embodiments, the coating may be relatively hydrophilic, such as a phosphorocholine compound. Additionally or alternatively, some or all of the filaments may have a coating or treatment (the same as the lubricious coating, or a different coating) that enhances blood compatibility and reduces the thrombogenic surface activity of the mesh (e.g., an antithrombogenic coating). In these and other embodiments, at least a portion of the mesh (or components thereof) can be made of other suitable materials.

In any of the foregoing embodiments, auxiliary fibrous materials may optionally be added to all or a portion of one, some, or all of the filaments of the mesh by weaving, tying, or other suitable permanent attachment methods. Moreover, some or all of the first and/or second meshes 102, 104 may comprise a radiopaque material. The methods of the present technology may be performed under fluoroscopy such that the radiopaque portions of the device 100 may be visualized by the physician to ensure proper neck coverage.

In use, the device 100 may be intravascularly delivered to the aneurysm cavity in a low-profile configuration within a delivery catheter (e.g., a microcatheter), such as elongated shaft 200. When contained within the delivery catheter, the portion of the device comprising the first mesh 102 may be positioned distal to the portion of the device comprising the second mesh 104, and the second mesh 104 is biased to position itself within the first mesh 102 during deployment. In some embodiments, the second mesh 104 is positioned within the first mesh 102 when constrained within the delivery catheter such that the first and second meshes 102, 104 are longitudinally aligned along at least a portion of their lengths. In any case, the distal opening of the shaft 200 may be positioned within the cavity, and the device 100 may be pushed from the distal opening of the delivery catheter into the aneurysm (or the catheter may be withdrawn while holding the device 100 generally stationary). As the device 100 is released from the catheter, first the first mesh 102 expands into apposition with an inner surface of the aneurysm wall, then the second mesh 104 is deployed (and expands) within the interior cavity of the first mesh 102.

Before or after the device 100 is detached from the manipulation member 202, an embolic material (e.g., one or more coils, one or more liquid embolics, etc.) may be delivered into the interior volume of the second mesh 104 through the same delivery catheter that delivered the first and second meshes 102, 104 and while the distal portion of the delivery catheter 200 is positioned within the interior cavity of the second mesh 104. When the physician is satisfied that the aneurysm is sufficiently occluded, the shaft 200 and manipulation member 202 can be withdrawn.

Example Methods of Manufacturing

Figure 4A:
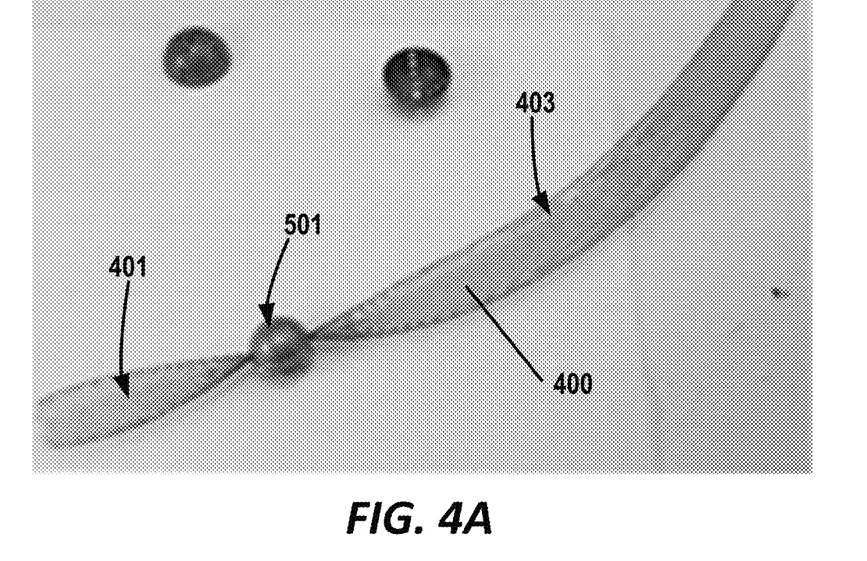
FIGS. 4A-4E show an example method for making an occlusive device of the present technology.
Figure 4B:
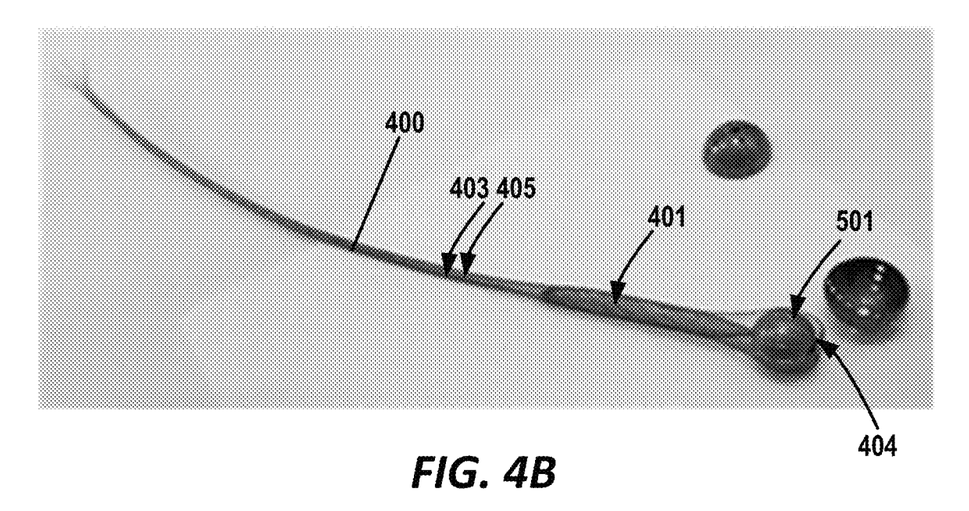

FIGS. 4A-4E depict an example for making the occlusive devices of the present technology. As shown in FIG. 4A, a tubular braid 400 may be inserted through a channel extending through a first spherical fixture 501 such that a first portion 401 of the braid 400 is proximal of the first fixture 501, a second portion 402 of the braid 400 (visible in FIG. 4E) is within the fixture 501, and a third portion 403 of the braid 400 extends distally from the first fixture 501. As shown in FIG. 4B, the third portion 403 of the braid 400 may then be inverted over the first fixture 501 (including the second portion 402 of the braid 400 therein) and the first portion 401 of the braid 400 such that the third portion 403 comprises a fourth portion 404 longitudinally aligned with the first fixture 501 and a fifth portion 405 coextensive with all or a portion of the first portion 401.

Figure 4C:
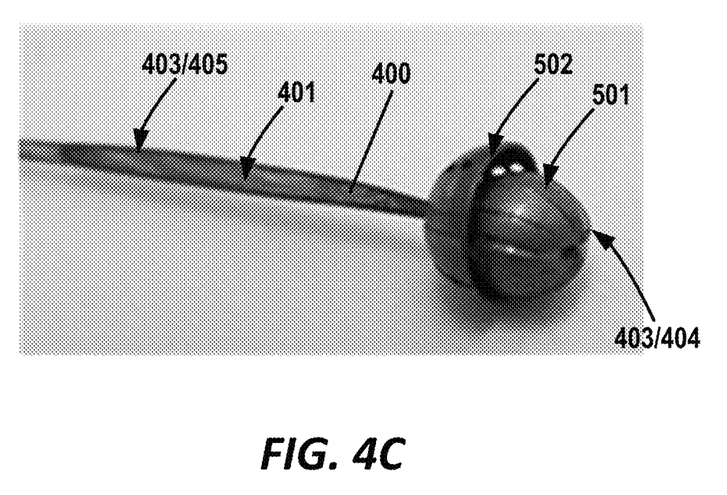

As shown in FIG. 4C, a second fixture 502 having an opening therethrough may then be threaded over the coextending first and fifth portions 401, 405 until all or a portion of the second fixture 502 is adjacent a proximal portion of the first fixture 501, thereby sandwiching the fourth portion 404 between the first and second fixtures 501, 502. In some embodiments, the shape defined by the inner surface of the second fixture 502 may complement the shape of the outer surface of the overlapping portion of the first fixture 501. In some embodiments, the shape defined by the inner surface of the second fixture 502 may be different and/or non-complementary to the shape of the outer surface of the overlapping portion of the first fixture 501.

Figure 4D:
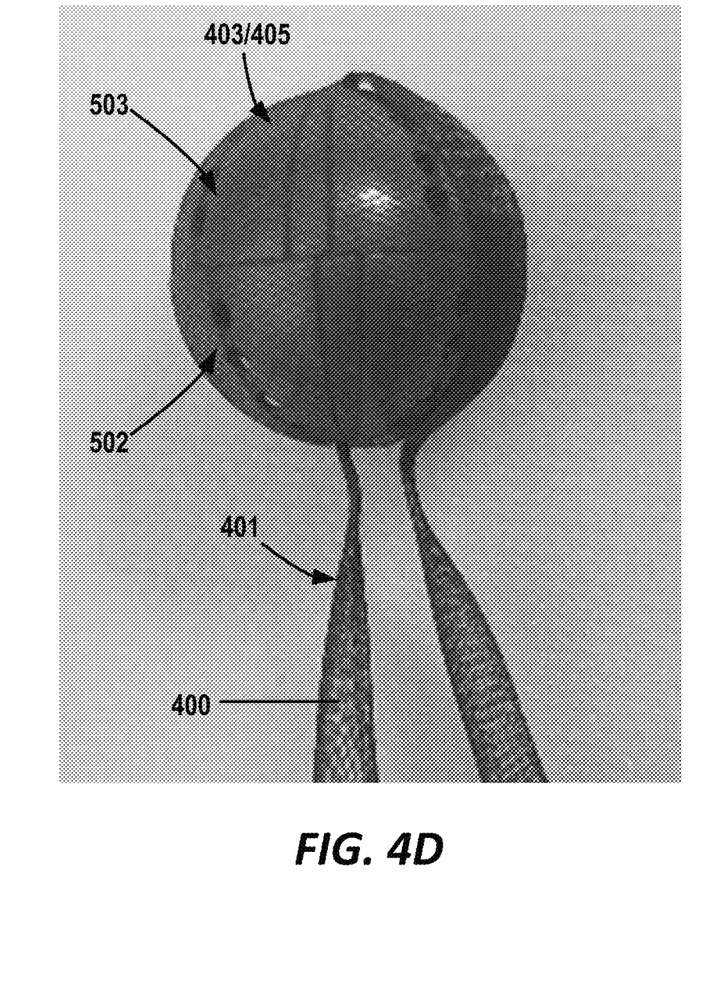

As depicted in FIG. 4D, a third fixture 503 may then be positioned over a distal portion of the first fixture 501 and the fourth portion 504 such that the fourth portion 504 (not visible in FIG. 4D) is sandwiched between the first and third fixtures 501, 503. In some embodiments, the shape defined by the inner surface of the third fixture 503 may complement the shape of the outer surface of the overlapping portion of the first fixture 501. In some embodiments, the shape defined by the inner surface of the third fixture 503 may be different and/or non-complementary to the shape of the outer surface of the overlapping portion of the first fixture 501.

The second and third fixtures 502, 503 may be arranged such that a distal surface of the second fixture 502 abuts and is in contact with a proximal surface of the third fixture 503. In some embodiments, the second and third fixtures 502, 503 may be adhered to one another. In some embodiments, the second and third fixtures 502, 503 may be disposed on the first fixture 501 such that the distal surface of the second fixture 502 is spaced apart from the proximal surface of the third fixture 503 (i.e., such that the second and third fixtures 502, 503 do not completely enclose the first fixture 501).

As shown in FIG. 4D, the method continues with everting the fifth portion 405 of the braid distally over the second and third fixtures 502, 503 (including the first fixture 501, second portion 402 of the braid 400, and fourth portion 404 of the braid 400 contained therein). The braid 400 may be crimped together at a distal portion of the fixture assembly, and brought together at a proximal portion of the fixture assembly at the proximal opening in the second fixture 502.

Figure 4E:
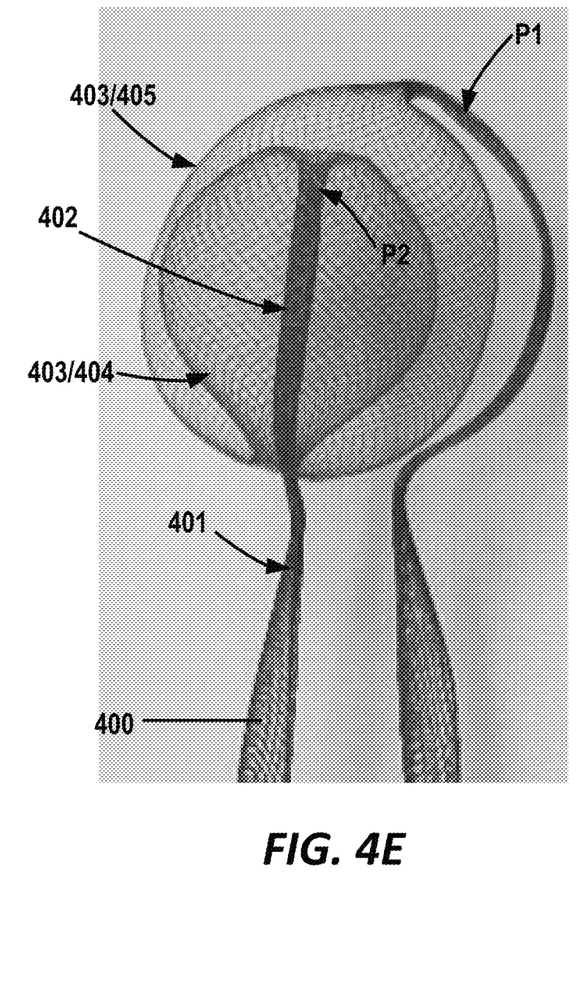

FIG. 4E shows the braid 400 after the braid and fixture assembly shown in FIG. 4D has been heat set and the fixture assembly is removed from the braid. As shown in FIG. 4E, at this stage the braid may comprise a distal tail extending distally from the fifth portion 405 (or outer mesh) and proximal tail comprising the second portion 402 and first portion 401. The braid 400 may be cut and the ends secured to one another at any location along the proximal and distal tail. For example, in some embodiments the braid 400 may be cut proximate the distal end portion of the fourth portion 404 (denoted by P2) within the inner cavity, and proximate the distal end portion of the fifth portion 405 at an exterior location. In these and other embodiments, the braid 400 may be cut between the expanded outer mesh and the beginning of the compressed distal tail, or at a location along the compressed distal tail (for example, as denoted by P1). It will be appreciated that other configurations are possible.

In some embodiments, the method further includes coupling a flexible elongated member to the inner mesh. In these and other embodiments, the method includes coupling a lead-in member to the outer mesh.

In the embodiments depicted by FIGS. 4A-4E, the first fixture 501 comprises a generally spherical shape and each of the second and third fixtures 502, 503 comprise a hollow hemisphere configured to fit over the spherical shape of the first fixture 501. In other embodiments, the first, second, or third fixtures may have different shapes or arrangements.

CONCLUSION

Although many of the embodiments are described above with respect to systems, devices, and methods for treating a cerebral aneurysm, the technology is applicable to other applications and/or other approaches. For example, the occlusive devices, systems, and methods of the present technology can be used to treat any vascular defect and/or fill or partially fill any body cavity or lumen or walls thereof, such as to treat parent vessel occlusion, endovascular aneurysms outside of the brain, arterial-venous malformations, embolism, atrial and ventricular septal defects, patent ductus arteriosus, and patent foramen ovale. Additionally, several other embodiments of the technology can have different states, components, or procedures than those described herein. It will be appreciated that specific elements, sub-structures, advantages, uses, and/or other features of the embodiments described can be suitably interchanged, substituted or otherwise configured with one another in accordance with additional embodiments of the present technology. A person of ordinary skill in the art, therefore, will accordingly understand that the technology can have other embodiments with additional elements, or the technology can have other embodiments without several of the features shown and described above with reference to FIGS. 1-4E.

As used herein, the terms "generally," "substantially," "about," and similar terms are used as terms of approximation and not as terms of degree, and are intended to account for the inherent variations in measured or calculated values that would be recognized by those of ordinary skill in the art.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. An occlusive device for treating an aneurysm, the device comprising:
   an expandable mesh having a proximal end portion and a distal end portion, the expandable mesh comprising:
      a first mesh defining a first cavity therein, the first mesh having a proximal end portion and a distal end portion, and
      a second mesh defining a second cavity therein, the second mesh having a proximal end portion and a distal end portion, wherein the second mesh is configured to be disposed within the first cavity when the expandable mesh is deployed within the aneurysm, and wherein the second mesh is biased to expand to a preset shape;
   a connection portion disposed at the distal end portion of the second mesh, the connection portion configured to detachably couple the expandable mesh to a delivery member; and
   a coil having a first end coupled to the distal end portion of the second mesh and a second end coupled to the proximal end portion of the first mesh, wherein the coil extends away from the second mesh within the first cavity,
   wherein the proximal end portion of the first mesh and the proximal end portion of the second mesh are continuous at a fold at the proximal end portion of the mesh, the fold surrounding an opening, and
   wherein the expandable mesh has a low-profile state for intravascular delivery to the aneurysm and an expanded state and, when the expandable mesh is implanted within the aneurysm in the expanded state, the second cavity is configured to receive and contain embolic material therein.

2. The device of claim 1, wherein the connection portion is disposed at least partially within the second cavity.

3. The device of claim 1, wherein the connection portion extends into the second cavity.

4. The device of claim 1 wherein the connection portion is disposed completely within the second cavity.

5. The device of claim 1, wherein a distal surface of the second mesh includes a depression that is concave towards the first cavity.

6. The device of claim 1, wherein the opening is configured to receive an elongated shaft therethrough, and wherein the elongated shaft is configured to receive the delivery member therethrough.

7. The device of claim 1, wherein, at least when the expandable mesh is in an expanded, unconstrained state, the distal end portion of the second mesh is spaced apart from the distal end portion of the first mesh such that the second end portion of the second mesh is free to axially stretch and compress independent of the first mesh.

8. The device of claim 1, wherein, when the expandable mesh is positioned within the aneurysm, the opening is aligned with the neck of the aneurysm.

9. The device of claim 1, wherein the proximal end portion of the expandable mesh does not include a hub.

10. An occlusive device for treating an aneurysm, the device comprising:
    a proximal end portion and a distal end portion, the proximal end portion comprising a proximal surface having an opening therethrough;
    an outer mesh defining an outer volume;
    an inner mesh defining an inner volume, wherein the outer and inner meshes meet at the opening, and wherein the inner mesh is biased to expand to a preset shape;
    a connector positioned at least partially within the inner volume at a location spaced apart from the proximal end portion of the device; and;
    a coil having a first end coupled to the connector and a second end coupled to the outer mesh, wherein the coil extends into the inner volume,
    wherein the device has a low-profile state for intravascular delivery to the aneurysm and an expanded state in which the inner mesh is disposed within the outer volume, and
    when the occlusive device is implanted within the aneurysm in the expanded state, the inner mesh is configured to receive embolic material within the inner volume.

11. The device of claim 10, wherein the opening is configured to receive an elongated shaft therethrough.

12. The device of claim 10, wherein, at least when the device is in an expanded, unconstrained state, a distal end portion of the inner mesh is spaced apart from a distal end portion of the outer mesh such that the distal end portion of the inner mesh is free to axially stretch and compress independent of the outer mesh.

13. The device of claim 10, wherein, when the device is positioned within the aneurysm, the opening is aligned with the neck of the aneurysm.

14. The device of claim 10, wherein the inner and/or outer meshes are generally ball-shaped.

15. The device of claim 10, wherein the proximal end portion of the device does not include a hub.

* * * * *